United States Patent [19]
Dieras et al.

[11] Patent Number: 5,702,360
[45] Date of Patent: Dec. 30, 1997

[54] ULTRASONIC SURGICAL KNIFE

[75] Inventors: Francis Dieras, Bordeaux; Jean-Luc Billard, Tresses, both of France

[73] Assignee: Satelec S.A., Merignac, France

[21] Appl. No.: 571,989

[22] PCT Filed: Jul. 8, 1994

[86] PCT No.: PCT/FR94/00853

§ 371 Date: Jan. 3, 1996

§ 102(e) Date: Jan. 3, 1996

[87] PCT Pub. No.: WO95/01754

PCT Pub. Date: Jan. 19, 1995

[30] Foreign Application Priority Data

Jul. 8, 1993 [FR] France ................ 93 08419

[51] Int. Cl.⁶ .................................. A61B 17/32
[52] U.S. Cl. .................. 604/22; 606/14; 606/169
[58] Field of Search .............. 606/169, 2.5, 14, 606/128; 601/2; 604/22

[56] References Cited

U.S. PATENT DOCUMENTS

| | | |
|---|---|---|
| 3,982,541 | 9/1976 | L'Esperance, Jr. . |
| 4,729,373 | 3/1988 | Peyman . |
| 4,808,153 | 2/1989 | Parisi .................. 606/169 X |
| 4,816,018 | 3/1989 | Parisi .................. 606/128 X |
| 5,413,556 | 5/1995 | Whittingham ........ 606/169 X |
| 5,474,530 | 12/1995 | Passafaro et al. ...... 606/169 X |

FOREIGN PATENT DOCUMENTS

| | | |
|---|---|---|
| 3 209 444 | 10/1982 | Germany . |
| 3 707 921 | 9/1987 | Germany . |
| 8 712 715 | 9/1987 | Germany . |
| WO 90/04362 | 5/1990 | WIPO . |
| WO 91/01692 | 2/1991 | WIPO . |

*Primary Examiner*—Michael H. Thaler
*Attorney, Agent, or Firm*—Young & Thompson

[57] ABSTRACT

A surgical knife comprising an ultrasonic generator (3) for ultrasonically vibrating an electrode or sonotrode (9) arranged at the front end of the knife and provided with an axial suction bore (19, 21). The surgical knife is characterized in that its back end comprises a member (31) for guiding a laser beam through the axial suction bore (19, 21) and onto a focal point (A) located beyond the front end of the sonotrode (9).

8 Claims, 1 Drawing Sheet

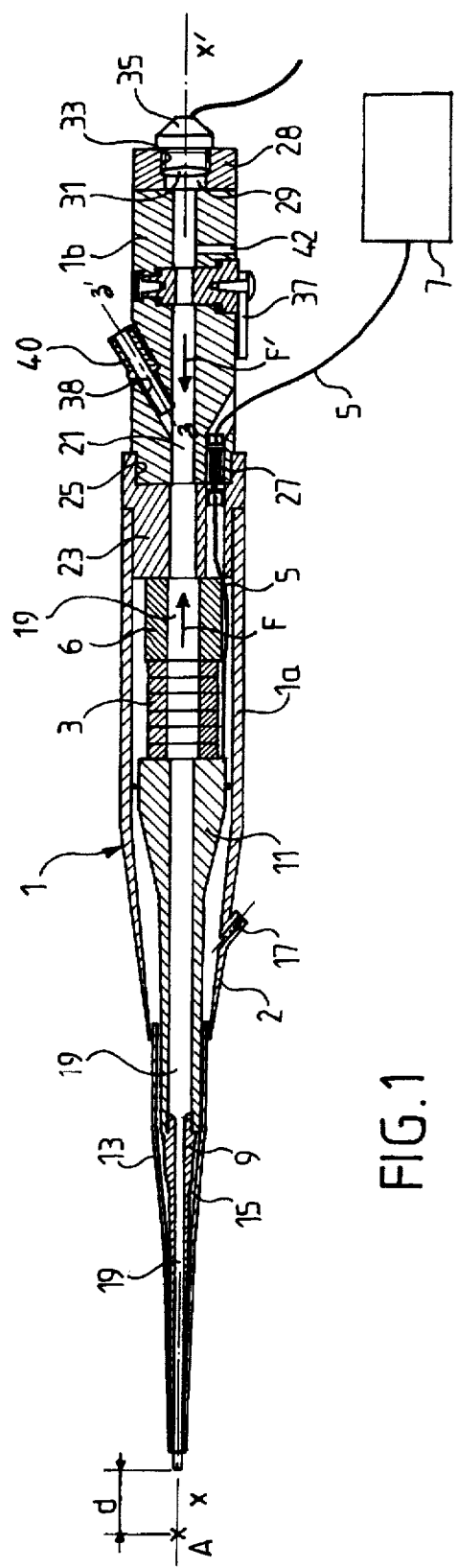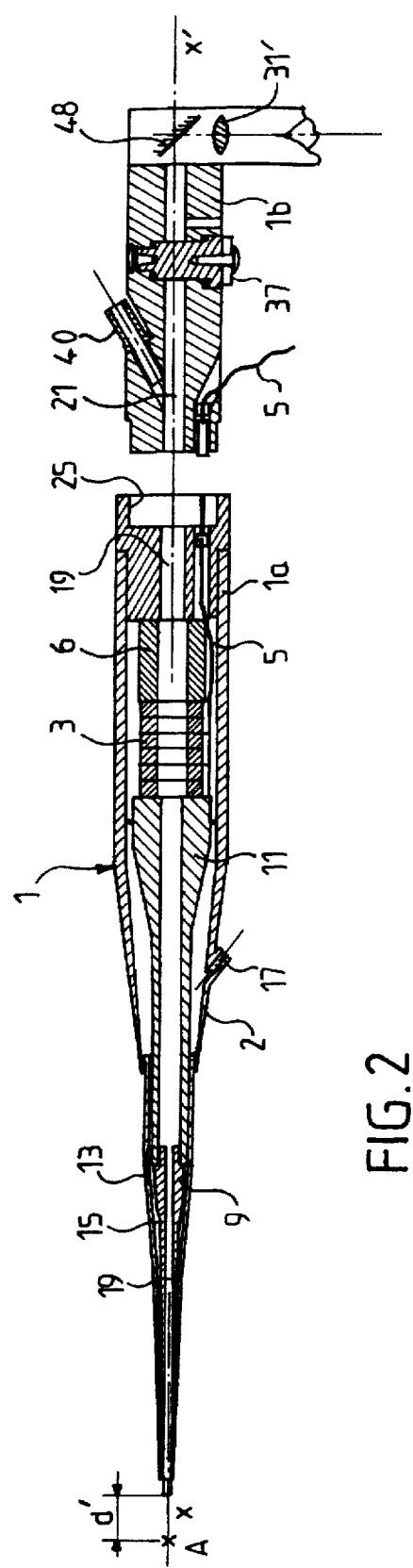
FIG.1
FIG.2

ULTRASONIC SURGICAL KNIFE

FIELD OF THE INVENTION

The present invention relates to a surgical knife, and more particularly an ultrasonic laser surgical knife adapted to perform cutting, dissection, vaporization and hemostasis of biological tissues.

BACKGROUND OF THE INVENTION

It is known that ultrasonic surgical knives are used in surgery to ensure the fragmentation of tissues. This fragmentation can be carried out in a selective manner, because of the phenomenon of cavitation which takes place on the more hydrated portions of the tissue, which cavitation phenomenon can be modulated by means of controlled irrigation and/or adjustment of the amplitude of the vibrations.

There is known, particularly from French patent No. 85.11106 in the name of the applicant, an ultrasonic surgical knife comprising irrigation means for the tissues to be fragmented and suction means permitting recovering both the fragmented tissues and the irrigation liquid.

It is also known that if the ultrasonic surgical knives are suitable for performing selective action on the tissues, their hemostatic power is limited to the very small vessels, so that the surgeon must have suitable means to effectuate cauterization of the tissues once the cutting of them has been carried out. Such a cutting operation therefore requires the use of a second instrument which, in the case of complicated operations, particularly in the case of endoscopic surgery, has substantial drawbacks, particularly because of the difficulty which exists to reposition precisely and exactly the cauterization instrument, such that its tool will be located in the initial position in which the cutting tool was located.

It has been proposed to carry out cauterization of the tissues by using the sonotrode of ultrasonic apparatus in the form of a high frequency electrode. The drawback of this technique is that the sonotrode, if it is of a shape suitable for propagation of ultrasound and the phenomenon of fragmentation of the tissues, has a profile which does not correspond to that which is needed for a cutting or hemostasis device.

There has also been used, as a surgical knife, lasers which carry out precise cutting of the tissues as well as hemostasis of these latter, but which have the drawback, when they cut, of not clearing the operating site. Moreover, these instruments have the drawback of producing smoke which obscures the operating field and limits accordingly the precision of the work of the surgeon.

There is known from the patent DE-A-2 707 921 an ultrasonic surgical knife provided with a laser whose radiation is guided by an optical filter to the forward end of the surgical knife.

SUMMARY OF THE INVENTION

The present invention has for its object to provide an ultrasonic surgical instrument, provided with laser cutting and cauterization means, which permits eliminating the debris of carbonization resulting from cutting effected by this latter as well as the smoke produced in the course of this cutting.

The present invention thus has for its object a surgical instrument comprising ultrasonic generator means adapted to subject a sonotrode disposed at its forward end, to ultrasonic vibratory movement, the surgical knife being traversed by at least one axial suction channel connecting its forward portion to its rearward portion, and comprising means to guide laser radiation to the forward end of the sonotrode, characterized in that it comprises means to direct said laser radiation through the suction channel and to focus it at a focal point located in front of the forward end of the sonotrode.

In an interesting embodiment of the invention, the surgical instrument comprises a suction channel opening into the central channel and closure means for this latter disposed upstream of the suction channel.

In another interesting embodiment of the invention, the surgical instrument comprises distribution means for a gaseous flow in the second axial suction channel, which open into this latter upstream of the suction conduit, and which create a gaseous current opposite the suction current.

BRIEF DESCRIPTION OF THE DRAWINGS

There will be described hereafter by way of non-limiting example, one embodiment of the present invention, with reference to the accompanying drawing, in which:

FIG. 1 is a longitudinal cross-sectional view of a first embodiment of the surgical instrument according to the invention.

FIG. 2 is a longitudinal cross-sectional view of a second embodiment of the surgical instrument according to the invention in the position of removing the handpiece.

DESCRIPTION OF THE PREFERRED EMBODIMENT

In FIGS. 1 and 2, the surgical instrument according to the invention comprises essentially a body 1 constituted by a forward portion 1a, or handpiece, and a rear portion 1b or a connector. The handpiece 1a terminates in its forward portion in a truncated conical head 2 which encloses a transducer 3 constituted by a stack of piezoelectric elements which are supplied with electric current by supply wires 5 connected to a high frequency current generator 7. In known manner, the transducer 3 is in contact on one side with a sonotrode 9, via an amplification member 11, and on the other side with a bearing member or "anvil" 6. The sonotrode 9 is surrounded by an envelope 13 which defines between itself and the sonotrode 9 an annular passage 15, supplied with irrigation liquid by a conduit 17 connected to an irrigation reservoir, not shown in the drawing.

The rear end of the handpiece 1a is closed by a plug 23 secured to the latter, which opens rearwardly in a cylindrical cavity 25 in which can be seated the rear portion of the body 1, or connector 1b, with interposition of sealing means not shown in the drawing. The handpiece 1a is traversed over all its length by an axial channel 19 which opens on one hand at the forward portion of the sonotrode 9 and, on the other hand, in the bottom of the cavity 25 of the plug 23.

Male/female electrical connection means 27 permit connecting the handpiece 1a and the connector 1b to the generator 7, by means of the supply wires 5. The connector 1b terminates at its rear end in a ring 28 traversed by an axial cavity 29 in which is housed a focusing lens 31. The axial cavity 29 comprises an internal screw thread 33 which is securable on a waveguide element 35 of a laser, not shown in the drawing. The connector 1b is traversed by an axial channel 21 which is located in the prolongation of the axial channel 19 and which is exactly aligned with this latter when the connector 1b is secured to the handpiece 1a. Under these circumstances, the surgical instrument is thus traversed end to end by the two channels 19 and 21.

A short distance downstream of the focusing lens 31, the second axial channel 21 is provided with a closure valve 37 adapted to occupy at least two positions, namely an open position (FIG. 1) in which the channels 19 and 21 are cleared such that the radiation emitted by the waveguide element 35 can traverse the channels 19 and 21, to be focused at a point A on the longitudinal axis xx' of the apparatus, located at a distance d in front of the sonotrode 9, and a closed position (FIG. 2) in which the radiation emitted by the laser is not admitted into the channel 21.

Downstream of the closure valve 37, the connector 1b is traversed by a screw-threaded orifice 38 with an axis zz' inclined to the axis xx' and which opens into the channel in which is screwed a nozzle 40 connected to the suction means (not shown in the drawing).

Between the focusing lens 31 and the closure valve 37 there is provided a conduit 42 of small diameter by which the channel 21 communicates with the exterior.

Under these circumstances, when it is desired to use the apparatus as a ultrasonic surgical instrument, the closure valve 37 is closed, so as to separate from the channel 21 the focusing lens 31, which protects the various projections, then the conduit 17 is supplied with irrigation liquid and the transducer 3 is excited by providing for its supply of electrical energy by means of the high frequency generator 7. The suction means are also actuated, which are connected to the nozzle 40, so as to be able to evacuate the residues resulting from the action of the surgical instrument.

When the operation is completed, and it is desired to cauterize the tissues, the closure valve 37 is opened, so as to clear the axial channels 19 and 21 and to permit the passage of the laser radiation focussed by the lens 31.

In the course of operation of the laser, the smoke produced by the action of this latter on the tissues is drawn off through the channels 19 and 21 to be evacuated through the opening 38 and the nozzle 40. The suction created by this latter induces a suction by the Venturi effect, which creates an air flow in the direction F', opposite the air flow F, so that the air flow F' forming an opposite flow prevents the smoke and other residues produced by the action of the laser beam to pollute the focusing lens 31.

Of course, the surgical instrument according to the invention could be used, not only to sever tissues by ultrasonic action and to cauterize by laser, but also to effect a direct cutting of the tissues with the aid of the laser beam.

The present invention is particularly interesting in that it permits the practitioner, particularly in the case of endoscopically controlled procedures, after having positioned the surgical instrument a first time and having effected an operation by ultrasound, to be able to avoid repositioning it a second time to effect a procedure with the laser, because the passage from one to the other is effected by simple swinging of control elements.

In the embodiment shown in the figures, the focusing means are constituted by a lens 31, but of course recourse could be had to any other different focusing means.

One could also, as shown in FIG. 2, use a laser producing a beam which will not be along the axis xx' of the axial channels 19 and 21, which is focused by means of a lens 31'. The beam is then directed along the axis xx' of the surgical instrument by means of a mirror 48, and the focusing is effected at a point A along the axis xx', at a desired given distance d' located in front of the end of the sonotrode 9.

We claim:

1. Surgical instrument having a forward portion, a rearward portion, and comprising ultrasonic generator means adapted to subject a sonotrode, disposed at a forward end of said surgical instrument, to an ultrasonic vibratory movement, the surgical instrument being traversed by at least one axial suction channel connecting the forward portion to the rearward portion, means for guiding laser radiation to a forward end of the sonotrode, focusing means for directing said laser radiation through the axial suction channel, and for focusing said laser radiation at a focal point located in front of the forward end of the sonotrode, and a secondary suction channel opening in the axial suction channel, adjacent said focusing means and creating a suction flow (F), and means for supplying a gaseous flow in the axial suction channel, which opens into said axial suction channel intermediate the secondary suction channel and the focusing means, and which creates a gas flow (F') opposite the flow of suction.

2. Surgical instrument according to claim 1, further comprising valve means disposed proximate a rear end of the surgical instrument for controlling closure of the axial suction channel.

3. Surgical instrument according to claim 1, wherein the means for supplying the gaseous flow in the axial suction channel comprise a conduit connecting the axial suction channel to the exterior, so as to cause said opposite flow by a Venturi effect.

4. Surgical instrument according to claim 1, wherein the surgical instrument is essentially constituted of two separate connectable elements, namely a forward handpiece element traversed by a first axial channel, and a rear connector element traversed by a second axial channel, aligned with the first axial channel, and wherein valve means and suction means are provided on the rear connector element.

5. Surgical instrument having a forward portion, a rearward portion, and comprising ultrasonic generator means adapted to subject a sonotrode, disposed at a forward end of said surgical instrument, to an ultrasonic vibratory movement, the surgical instrument being traversed by at least one axial suction channel connecting the forward portion to the rearward portion, means for guiding laser radiation to a forward end of the sonotrode, focusing means for directing said laser radiation through the axial suction channel, and for focusing said laser radiation at a focal point located in front of the forward end of the sonotrode, a secondary suction channel opening in the axial suction channel, adjacent said focussing means, creating a suction flow (F), and valve means disposed intermediate said secondary suction channel and said focusing means, for controlling closure of the axial suction channel.

6. Surgical instrument according to claim 5, further comprising means for supplying a gaseous flow in the axial suction channel, which opens into said axial suction channel intermediate the secondary suction channel and the focusing means, and which creates a gas flow (F') opposite the flow of suction.

7. Surgical instrument according to claim 6, wherein the means for supplying the gaseous flow in the axial suction channel comprise a conduit connecting the axial suction channel to the exterior, so as to cause said opposite flow by a Venturi effect.

8. Surgical instrument according to claim 5, wherein the surgical instrument is essentially constituted of two separate connectable elements, namely a forward handpiece element traversed by a first axial channel, and a rear connector element traversed by a second axial channel, aligned with the first axial channel, and wherein suction means and the valve means are provided on the rear connector element.

* * * * *